US007189306B2

(12) United States Patent
Gervais

(10) Patent No.: US 7,189,306 B2
(45) Date of Patent: Mar. 13, 2007

(54) PROCESS OF TREATING LIGNOCELLULOSIC MATERIAL TO PRODUCE BIO-ETHANOL

(76) Inventor: Gibson W. Gervais, Box 262, Amherstburg, Ontario (CA) N9V 2Z2

( * ) Notice: Subject to any disclaimer, the term of this patent is extended or adjusted under 35 U.S.C. 154(b) by 327 days.

(21) Appl. No.: 10/373,588

(22) Filed: Feb. 24, 2003

(65) Prior Publication Data

US 2004/0016525 A1 Jan. 29, 2004

Related U.S. Application Data

(60) Provisional application No. 60/358,863, filed on Feb. 22, 2002.

(51) Int. Cl.
*D21B 3/02* (2006.01)
*D21C 1/36* (2006.01)

(52) U.S. Cl. ............... 162/21; 162/90; 162/14; 162/16; 162/78; 162/79; 162/65; 162/68; 162/56; 435/161

(58) Field of Classification Search ............ 162/21, 162/22, 65, 78, 90, 79, 68, 14–16, 18, 56, 162/24, 29; 426/447, 448; 127/36, 37; 435/161; 536/1.1
See application file for complete search history.

(56) References Cited

U.S. PATENT DOCUMENTS

| 513,586 A | 1/1894 | Martin |
| 3,719,552 A | 3/1973 | Farley et al. .............. 162/65 |
| 3,966,607 A | 6/1976 | Gaynor et al. ............ 210/137 |
| 4,136,207 A | 1/1979 | Bender ..................... 426/510 |

(Continued)

FOREIGN PATENT DOCUMENTS

WO    WO 91/10740    7/1991

(Continued)

OTHER PUBLICATIONS

Stake Technology Ltd. web pp. (2), "Steam Explosion Technology", admitted as prior art.

(Continued)

*Primary Examiner*—Eric Hug
(74) *Attorney, Agent, or Firm*—Butzel Long

(57) ABSTRACT

This invention relates to a process of treating a lignocellulosic material to produce bio-ethanol. The process includes the steps of: (a) exposing the lignocellulosic material to conditions including a pH not less than about 8, and steam at a first pressure, to produce a step (a) product; (b) explosively discharging the step (a) product to a second pressure less than the first pressure to produce a step (b) product; and (c) further processing the step (b) product to produce bio-ethanol and other co-products. In another embodiment, the invention relates to a conical auger fractionation column. The fractionation column includes a column body having an input and an output. A conical filter is positioned inside the column body, the filter having a larger diameter end directed toward the input and a smaller diameter end directed toward the output. A conical auger is positioned inside the conical filter, the conical auger having an outer diameter which is approximately the same as an inner diameter of the conical filter. The auger and filter are adapted to cooperate to separate cellulosic solids from a liquid stream in a process of producing bio-ethanol from a lignocellulosic material.

17 Claims, 3 Drawing Sheets

U.S. PATENT DOCUMENTS

| | | | |
|---|---|---|---|
| 4,186,658 A | 2/1980 | Brown | 100/148 |
| 4,196,043 A | 4/1980 | Singh | 162/30 |
| 4,372,812 A | 2/1983 | Phillips et al. | 162/40 |
| 4,412,485 A | 11/1983 | Brown | 100/117 |
| 4,461,648 A | 7/1984 | Foody | 127/37 |
| 4,632,795 A | 12/1986 | Huber et al. | 264/115 |
| 4,649,113 A | 3/1987 | Gould | 435/165 |
| 4,729,817 A | 3/1988 | Francis et al. | 162/65 |
| 4,798,651 A | 1/1989 | Kokta | 162/22 |
| 4,842,877 A | 6/1989 | Tyson | 426/271 |
| 4,881,690 A | 11/1989 | Maier | 241/82.3 |
| 4,908,099 A * | 3/1990 | DeLong | 162/21 |
| 4,915,308 A | 4/1990 | Koenig | 241/152 |
| 4,947,743 A | 8/1990 | Brown et al. | 100/45 |
| 4,966,650 A | 10/1990 | DeLong et al. | 162/14 |
| 5,122,228 A | 6/1992 | Bouchette et al. | 162/4 |
| 5,198,074 A * | 3/1993 | Villavicencio et al. | 162/15 |
| 5,234,400 A | 8/1993 | Kluge | 494/54 |
| 5,296,136 A | 3/1994 | Abel | 210/158 |
| 5,545,418 A | 8/1996 | Iritani et al. | 426/53 |
| 5,547,692 A | 8/1996 | Iritani et al. | 426/53 |
| 5,558,433 A | 9/1996 | Gheorghita | 366/76.4 |
| 5,693,296 A | 12/1997 | Holtzapple et al. | 423/165 |
| 5,705,216 A | 1/1998 | Tyson | 426/478 |
| 5,777,086 A | 7/1998 | Klyosov et al. | 530/500 |
| 5,795,479 A | 8/1998 | Vogt et al. | 210/603 |
| 5,846,787 A | 12/1998 | Ladisch et al. | 435/99 |
| RE36,023 E | 1/1999 | Koenig | 241/260.1 |
| 5,865,898 A | 2/1999 | Holtzapple et al. | 127/37 |
| 5,916,415 A | 6/1999 | Miller | 162/65 |
| 6,048,458 A | 4/2000 | Vogt et al. | 210/603 |
| 6,090,595 A | 7/2000 | Foody et al. | 435/99 |
| 6,103,059 A | 8/2000 | Call | 162/65 |
| 6,162,324 A | 12/2000 | Miller | 162/57 |
| 6,165,318 A | 12/2000 | Paren et al. | 162/76 |
| 6,221,207 B1 | 4/2001 | Forslund et al. | 162/47 |
| 6,365,732 B1 | 4/2002 | Van Thorre | 536/84 |
| 6,379,527 B1 | 4/2002 | Vogt et al. | 205/560 |
| 6,409,841 B1 * | 6/2002 | Lombard | 127/37 |
| 2001/0020520 A1 | 9/2001 | Hu et al. | 162/9 |
| 2001/0025695 A1 | 10/2001 | Patt et al. | 162/72 |
| 2001/0050152 A1 | 12/2001 | Forslund et al. | 162/65 |
| 2003/0176669 A1 | 9/2003 | Van Thorre | 536/1.11 |

FOREIGN PATENT DOCUMENTS

WO    WO 96/25553    8/1996

OTHER PUBLICATIONS

IEA Bioenergy Newsletter, "Biotechnology for the Conversion of Lignocellulosics to Ethanol", May 1998, pp. 1 and 9 of 27.

TAPPI 1996, "Continuous Steam Explosion Pulping, a Viable Alternative . . . ", pp. 1-10 of 10 and pp. 1-2 of 2 (references).

TAPPI 1998, "Steam Explosion Pulping of Bagasse . . . ", pp. 1-13 of 13.

TAPPI 1997, "Continuous Steam Explosion Pulping: Process Optimization . . . ", pp. 1-13 of 13.

* cited by examiner

PROCESS OF TREATING LIGNOCELLULOSIC MATERIAL TO PRODUCE BIO-ETHANOL

CROSS-REFERENCE TO RELATED-APPLICATION

This application claims the benefit of U.S. provisional application Ser. No. 60/358,863, filed Feb. 22, 2002.

BACKGROUND OF THE INVENTION

This invention relates in general to processes for producing bio-ethanol, and in particular to an improved process for producing bio-ethanol from a lignocellulosic material.

Since the development of internal combustion engines and automobile mass production by Henry Ford there has been interest in ethanol. Clean burning, higher octane than gasoline, ethanol had been Ford's original choice of fuel for the Model "T", but then (and for the past 75 years) fossil fuels became the dominant source of portable energy for industry and consumers. The result has been a polluted world, dependance on foreign nations for energy supplies and ever increasing costs as fossil fuel sources are depleted.

Ethanol, a naturally renewable fuel source, has generated immense interest over the past 10–15 years. The move to ethanol-enriched cleaner fuels, which eliminate or reduce the polluting and carcinogenic additives required to enhance gasoline, has produced a huge and increasing demand for ethanol around the world. In much of North America, 10% ethanol in gasoline is the standard, and in other countries such as Brazil, E-85 (85% or more ethanol) is the new standard. Clearly, as fossil fuels disappear, this new technology is the energy source of future.

With the increasing cost of oil and gasoline and the development of other ethanol markets, corn- and grain-based ethanol production has gradually become commercially viable. There is tremendous growth forecasted in this area over the next 10 years as the gradual fuel conversion to E-85 and environmental-based demands for ethanol increase. Most Canadian ethanol plants are in the process of dramatically expanding their production facilities.

Presently, almost all bio-ethanol production facilities in North America are corn- or grain-based. They grind up starch/carbohydrate rich corn/grain, treat this with a complex process to break this substrate into sugars (primarily glucose), and then ferment the sugars into ethanol (with the by-product of $CO_2$) for industrial/commercial and medical uses.

The technology advances in these corn/grain production based industries have gradually reduced the, cost of ethanol to current levels, but they have reached a "wall" which is related to the availability and cost of their "substrate", corn or grain. A major expense and uncontrollable factor will always be the price of corn/grain and the fact that the process substrate is "food" for animals or humans and in limited supply. Certainly, the supply is far too limited to allow for the competing worldwide demand for both food and bio-ethanol in the future.

These conclusions have prompted nationwide efforts in Canada and the USA over the past 10 years to investigate and develop technology to produce ethanol from lignocellulosic biomass (e.g., wood chips, leaves, corn stover, straw, bagasse, rice straw, and municipal cellulosic waste). In a typical lignocellulosic biomass process, substrate primarily composed of cellulose is ground up and then pre-treated (usually with acid) to break down the cellulose and separate the three main components of wood (cellulose, hemi-cellulose and lignin). These components are then acted upon by catabolic enzymes to form a fermentable mixture of glucose and xylose (the basic component of hemi-cellulose), and this is then fermented and distilled to create ethanol.

The intrinsic advantages of this process are that there is a virtually unlimited supply of lignocellulosic biomass of many types, it is fully renewable and natural, and it is cheap. In fact, many potential sources of lignocelluosic biomass actually generate revenue for the process due to their present disposal costs. Bio-ethanol production is relatively environmental friendly, as much of this feedstock material is burned, ploughed under or composted. However, based on present technologies, the current cost/gallon for bio-ethanol remains high in relation to fossil fuels. Lignocellulosic bio-ethanol production simply costs too much, because the basic "substrate" materials (wood, non-woody lignocellulosic feedstock) are difficult and expensive to break down into fermentable materials. Consequently, there are presently no commercial lignocellulosic biomass to ethanol plants in North America.

There is an extensive patent literature relating to de-lignification of lignocellulosic materials, predominantly relating to applications in the pulp and paper industry. For example, bleaching of lignocellulosic materials in the presence of oxygen and peroxide has been described in U.S. patents such as Farley U.S. Pat. No. 3,719,552, Tyson U.S. Pat. No. 4,842,877, Phillips U.S. Pat. No. 4,372,812, Paren U.S. Pat. No 6,165,318, Francis U.S. Pat. No. 4,729,817, Miller U.S. Pat. No. 6,162,324, Forslund U.S. Pat. No. 6,221,207, Call U.S. Pat. No. 6,103,059, Miller U.S. Pat. No 5,916,415, Gould U.S. Pat. No. 4,649,113, Singh U.S. Pat. No. 4,196,043, Foody U.S. Pat. No. 6,090,595, Holtzapple U.S. Pat. No. 5,865,898, Ladisch U.S. Pat. No. 5,846,787, Klyosov U.S. Pat. No. 5,777,086, and in U.S. patent applications such as Forslund 2001050152, and Pat 20010025695. The described processes focus on improvement in de-lignification during bleaching of paper pulps with retention of viscosity index (indicative of cellulose strand integrity/predictive of paper strength). The primary goal of these de-lignification process improvements has been to avoid the negative aspects of various pretreatments used in the pulp and paper industry, specifically to de-lignify with reduced disruption of the cellulose polymer structure. Most of this work is not related to pretreatment during bio-ethanol production.

SUMMARY OF THE INVENTION

This invention relates to a process of treating a lignocellulosic material to produce bio-ethanol. The process includes the steps of: (a) exposing the lignocellulosic material to conditions including a pH not less than about 8, and steam at a first pressure, to produce a step (a) product (for example, the reaction product in the reaction chamber of a steam explosion apparatus); (b) explosively discharging the step (a) product to a second pressure less than the first pressure to produce a step (b) product (for example, the product after steam explosion in a steam explosion apparatus); and (c) further processing the step (b) product to produce bio-ethanol and other co-products.

In another embodiment, the invention relates to a process of treating a lignocellulosic material to produce bio-ethanol. The process includes the steps of: (a) exposing the ligno-cellulosic material to conditions including a pH not less than about 8, and steam at a first pressure, to produce a step-(a) product; (b) explosively discharging the step (a) product to a second pressure less than the first pressure to produce a slurry containing cellulosic solids; (c) passing the slurry through a fractionation device to separate the cellulosic solids from a liquid stream, the device increasing pressure on the separated solids as the solids pass through the device to increase separation efficiency; and (d) further processing the cellulosic solids and the liquid stream to produce bio-ethanol and other co-products.

In another embodiment, the invention relates to a conical auger fractionation column. The fractionation column includes a column body having an input and an output. A conical filter is positioned inside the column body, the filter having a larger diameter end directed toward the input and a smaller diameter end directed toward the output. A conical auger is positioned inside the conical filter, the conical auger having an outer diameter which is approximately the same as an inner diameter of the conical filter. The auger and filter are adapted to cooperate to separate cellulosic solids from a liquid stream in a process of producing bio-ethanol from a lignocellulosic material.

Various advantages of this invention will become apparent to those skilled in the art from the following detailed description of the preferred embodiments, when read in light of the accompanying drawings.

DETAILED DESCRIPTION OF THE PREFERRED EMBODIMENTS

Figure 1:
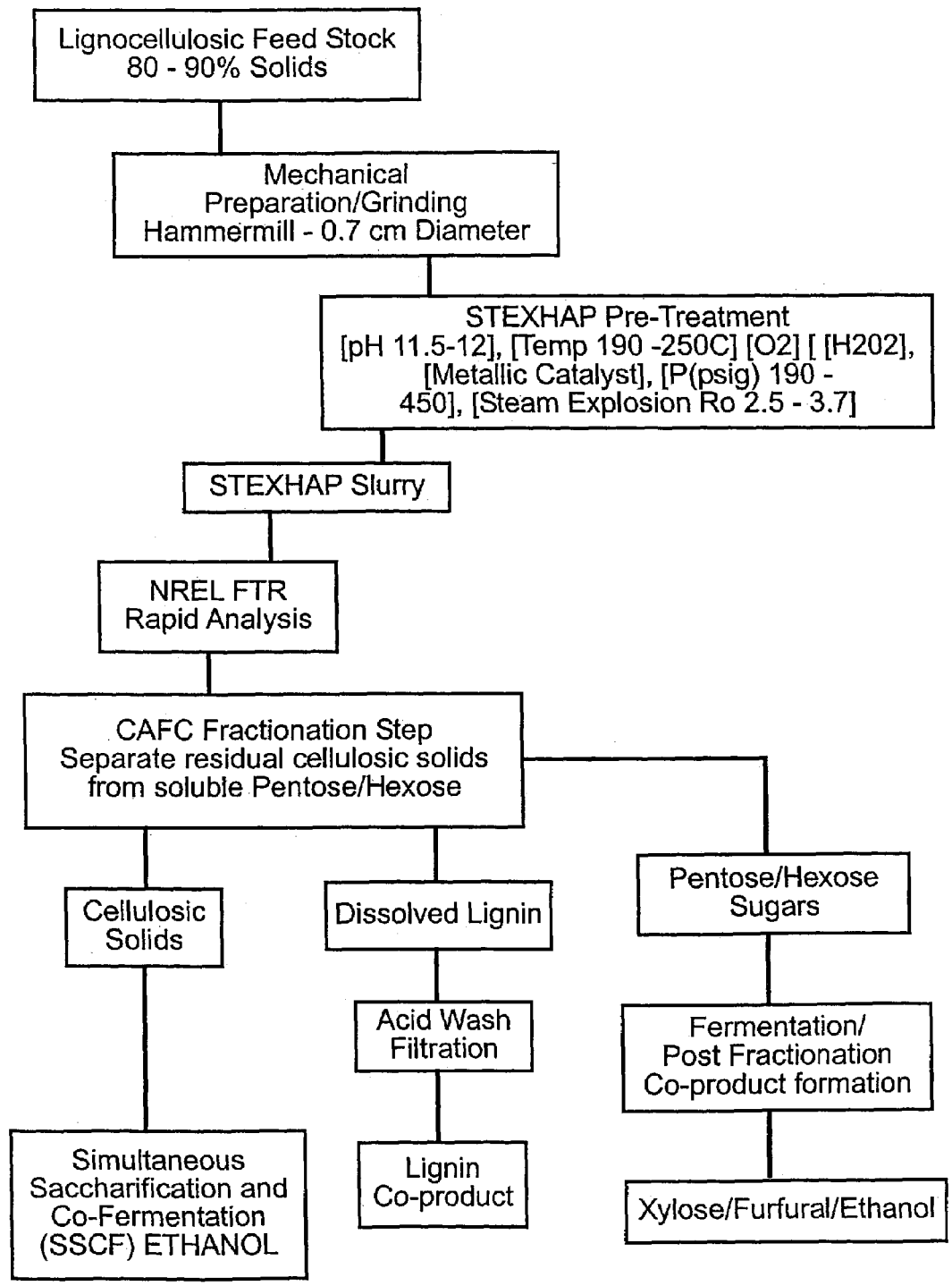
FIG. 1 is a flow diagram of a preferred process of treating a lignocellulosic material to produce bio-ethanol in accordance with the present invention.

This invention relates to an improved process of treating a lignocellulosic material to produce bio-ethanol. Any suitable lignocellulosic material can be used in the invention. As shown in FIG. 1, a preferred lignocellulosic feed stock contains from about 80% to about 90% solids by weight. Preferably, the lignocellulosic material is lignocellulosic biomass, such as wood chips, leaves, corn stover, straw, bagasse, rice straw, municipal cellulosic waste, and/or other known lignocellulosic biomass.

As shown in FIG. 1, preferably the lignocellulosic material is prepared for the process by mechanical grinding. Any suitable grinding equipment and process can be used. In one embodiment, the material is ground with a Hammermill to an average particle size of about 0.7 cm diameter.

The lignocellulosic material is then exposed to conditions including a pH not less than about 8, and steam at a first pressure. The alkaline pH helps to break down the lignocellulosic material without the formation of undesirable byproducts. Preferably, the pH is not less than about 11, and more preferably from about 11.5 to about 12. The alkaline pH can be achieved by the addition of any suitable alkaline material, such as NaOH or $CaCO_3$. Preferably, the conditions also include a temperature not lower than about 190° C., and more preferably from about 190° C. to about 250° C. Preferably, the conditions also include hyperbaric oxygen and peroxide. Optionally, any suitable catalyst can be used, including a metallic catalyst such as $Fe(OH_3)$, ZN, $Cr_2O_3$, $TiO_2$, $TiCl_3$, $NaMnO_4$, or a transition metal catalyst. These conditions are preferably maintained for a time of from about 1 minute to about 5 minutes. The focus of this treatment is on optimal de-lignification of the material and the provision of the maximum number of cellulase binding sites (theoretically reducing the amount and increasing the efficiency of enzyme action on the substrate).

The de-lignified material is then explosively discharged to a second pressure less than the first pressure. The exploded product usually consists of a slurry containing cellulose polymers, solubilized lignin, pentose compounds and other materials. Preferably, the first pressure is a pressure of from about 190 psig to about 450 psig, and more preferably from about 350 psig to about 450 psig. Preferably, the second pressure is atmospheric pressure.

The flow diagram in FIG. 1 shows some of these preferred process conditions in the box entitled "STEXHAP Pre-Treatment", where STEXHAP is an acronym for "Steam Explosion Hot Alkaline Peroxide". The increased severity of the treatment conditions would be detrimental to the production of paper where integrity of the long cellulose strands and limited saccharification is beneficial. In contrast to the process conditions used for pulp and paper manufacturing, the process conditions of the present invention are aimed at disrupting the lignocellulosic structure and breaking up the long cellulose polymers, producing more polysaccharides and reducing the required amount of cellulase enzymes.

Figure 2:
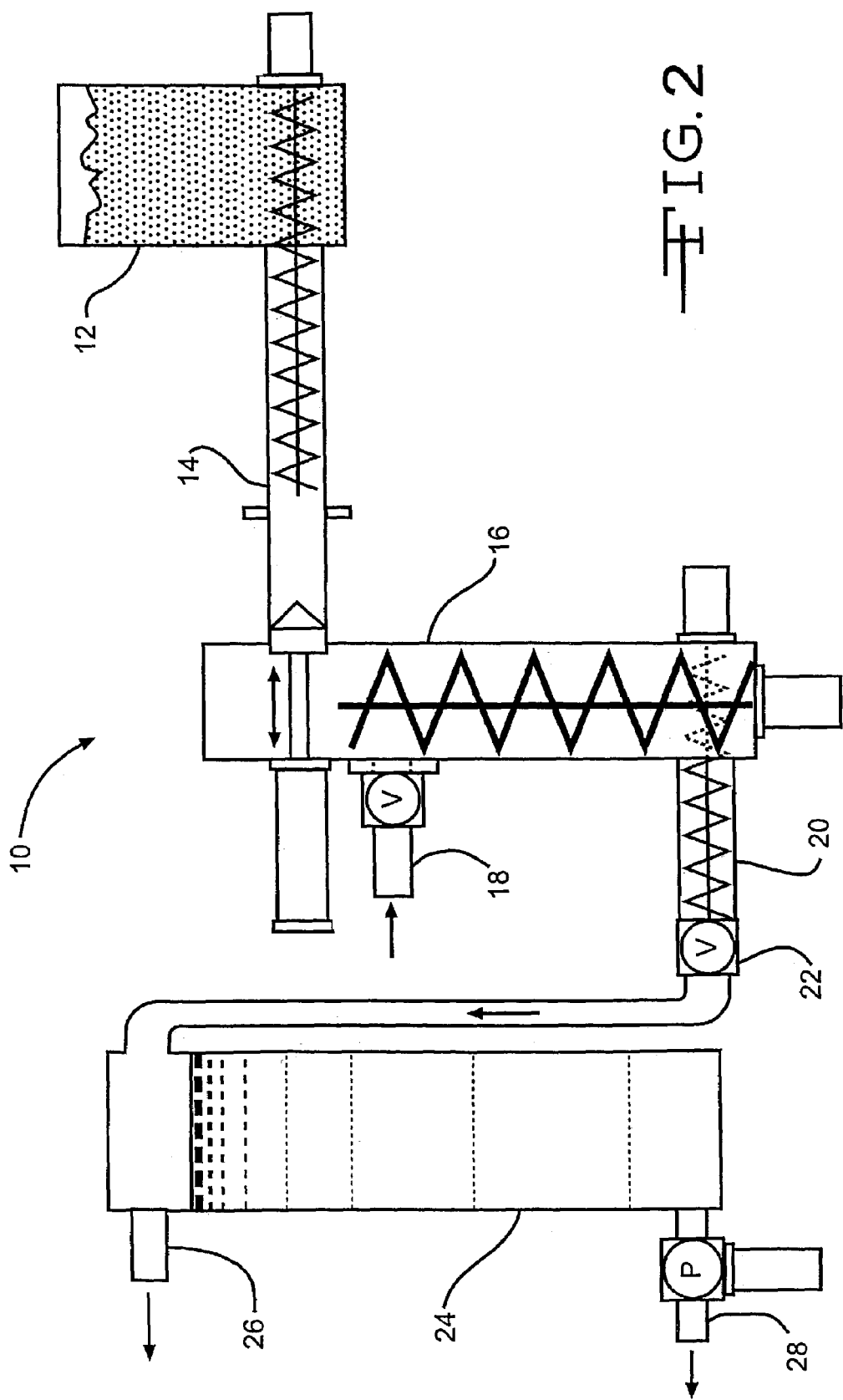
FIG. 2 is side elevational view, partly in cross-section and partly in perspective, of a continuous steam explosion apparatus for use in the process of the invention.

The lignocellulosic material is exposed to these conditions in a reaction chamber of a steam explosion apparatus. Any suitable steam explosion apparatus can be used in the invention, including batch or continuous apparatuses. Preferably, the apparatus is a continuous steam explosion apparatus manufactured by Stake Technology Ltd., Norval, Ontario Canada. FIG. 2 illustrates such an apparatus 10. The lignocellulosic material and any added chemical(s) are introduced into a feed hopper 12. The material flows into a co-ax feeder 14 where a reciprocating piston compresses the material into a dense plug, thereby maintaining operating pressure within the apparatus. The material then flows into a digester 16 into which high pressure steam is introduced through an inlet 18. The material remains in the digester for a predetermined dwell time. The material then flows to a discharge screw 20 with a blow valve 22, where the material is explosively discharged to atmospheric pressure. The resulting material is in the form of a slurry. Optionally, the slurry then flows through a blow tank 24. Condensed steam flows through an upper outlet 26, and the processed material is pumped through a lower outlet 28 for further processing.

The steam explosion produces both a mechanical and chemical change in the lignocellulosic material which is related to the steam treatment reaction ordinate defined as:

$Ro=t'\exp[(T-100)/14.75]$, where Ro=the severity factor in minutes,
t=the residence time in minutes, and
T=the steam temperature in degrees C.

Preferably, the steam explosion used in the process of the invention has a Ro of from about 2.5 to about 3.7, and more preferably from about 3.0 to about 3.7.

The steam explosion process disrupts the crystalline cellulose structure causing deacetylation and auto-hydrolysis of the hemicellulose to xylose at the moment of steam explosion. Under these conditions including high pH, lignin is also melted so that the remaining material becomes a slurry of cellulose and polysaccharides potentially available for enzymatic digestion as well as solublized lignin and pentose compounds. Some volatile organics such as furfural are produced during steam explosion possibly due to the release of acetic acid during auto-hydrolysis. Continuous steam explosion allows high volume bio-mass pre-treatment at very low operational costs. The furfural production during steam explosion is probably related to release of acetic acid during autohydrolysis as a degradation product of the five carbon sugars. Under the proposed conditions (STEXHAP) for this process, it is projected that auto-hydrolysis will result in a minimal furfural production and that this compound will remain in solution at the time of fractionation of the slurry (described below). This is significant because furfural is a known inhibitor of the combined saccharification/fermentation process SSCF which will subsequently be applied to the de-lignified bio-mass. Lignin is also solubilized at high pH and the temperatures described, enhancing separation of the lignin from the cellulosic material.

The slurry from the STEXHAP process steps is then further processed to produce bio-ethanol. Preferably, the slurry is first passed directly from the steam explosion process to a fractionation device to separate the cellulosic solids from a liquid stream. As shown in FIG. 1, the STEXHAP slurry is passed to a CAFC fractionation step. Optionally, the slurry can be analyzed by NREL FTR or another suitable method before the fractionation.

Figure 3:
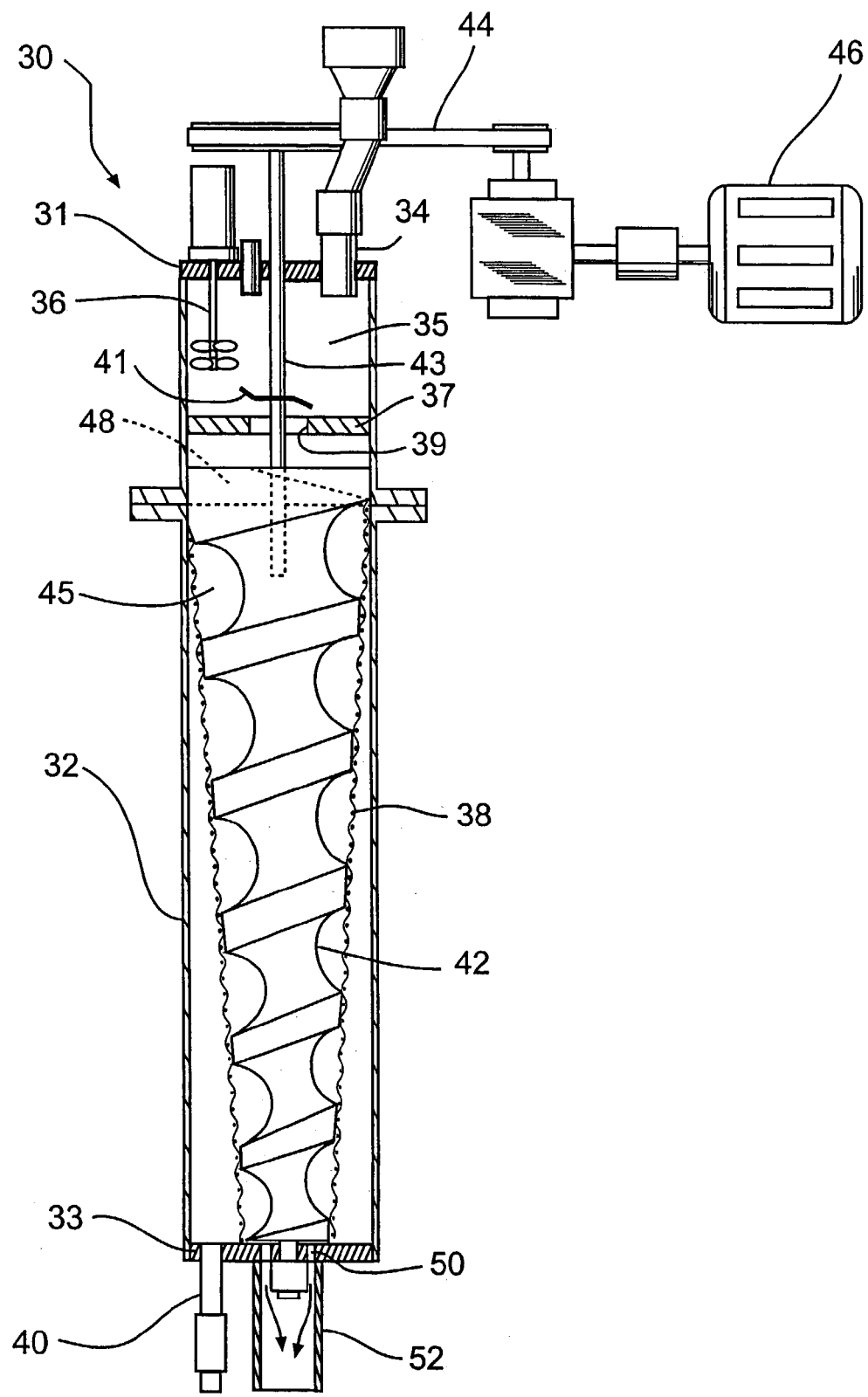
FIG. 3 is a side elevational view, partly in cross-section, of a conical augur fractionation column for use in the process of the invention.

FIG. 3 illustrates a preferred conical auger fractionation column 30 (CAFC) for use in fractionating the slurry. The fractionation column 30 includes a cylindrical column body 32 having a top 31 and a base 33. The column body can be made from any suitable material; in one embodiment, the cylinder portion of the body consists of an acrylic tube having an inner diameter of about 7.5 inches, and the top and base of the body are circular pieces of metal or plastic. An input pipe 34 is connected to the top 31 of the column body to allow the slurry to be-introduced into the interior of the body. The fractionation column 30 includes a mixing chamber 35 within the top part of the column body 34, between the top 31 of the column body and a lower mixing chamber wall 37. A mixing chamber hole 39, which can be varied in size, is located in the mixing chamber wall 37. Preferably, the fractionation column 30 includes an agitation device 36 to mix the slurry during addition of water, catalysts, enzymes or other compounds to enhance the separation of the slurry fractions during passage through the column. The fractionation column can also include a deflector paddle 41 connected to a central shaft 43 of the column.

The fractionation column 30 increases the pressure on the separated solids as the solids pass through the device to increase separation efficiency. The fractionation column can include any suitable structure to achieve this benefit. In the illustrated embodiment, the fractionation column includes a conical filter 38 inside the column body. The filter has a larger diameter end directed toward the top 31 of the column and a smaller diameter end directed toward the base 33 of the column. The filter can be made from any suitable material; for example, it can be made from a screen or a solid sheet having pores of a suitable diameter through which liquid is forced. In a preferred embodiment, the filter is made from a 40 mesh or 50 mesh stainless steel screen. The illustrated fractionation column also includes a conical auger 42 inside the conical filter. The conical auger has an outer diameter which is approximately the same as an inner diameter of the conical filter. The conical auger can be made from any suitable material, including construction from a solid sheet of metal or plastic with multiple holes of a suitable diameter. The conical auger 42 can also have any suitable structure to allow the slurry to pass downward between the auger and the filter 38. In one embodiment, the conical augur has a leading edge or blade which extends to the margin of the filter cone from the central shaft 43, similar to the leading edge of a snail shell. The conical augur has an opening area 48 at the top through which the slurry passes downward. The conical auger 42 is connected to the central shaft 43 for rotation. The fractionation column includes a pulley 44 to rotate the central shaft and the auger, and a motor 46 to drive the pulley.

In operation, the slurry enters the fractionation column 30 through the input pipe 34 and flows into the mixing chamber 35. The slurry then passes out of the mixing chamber through the hole 39 and drops down into the opening 48 of the conical auger 42. The slurry flows down into the top of the fractionation chamber 45 under the upper edge of the auger. As the auger turns, additional slurry material is forced down into the chamber under the leading edge of the auger blade. The conical auger 42 is rotated within the conical filter 40, forcing the liquids of the slurry to flow out through the pores of the screen while the solids remain within the screen. Due to the reducing diameter of the auger and filter, the rotation of the auger, and the force of gravity, the device concentrates filtered solids under increasing hydraulic pressure towards the base of the column, increasing filtration efficiency. Advantageously, as the auger turns within the filter it clears away solids from the interior surface of the filter, keeping the filter clean and unblocked for better filtering efficiency.

The filtered cellulosic solids pass through one or more exit holes 50 at the bottom of the conical auger and into a solids output conduit 52. The number and size of the exit hole(s) can be varied to control the residency time of the slurry within the filter, affecting the extent of dehydration of the slurry and the degree of filtration of the water-soluble elements. The mesh size of the screen can also be varied for this purpose. The rotation of the auger, in conjunction with the reducing diameter of the column and the outlet flow obstruction through the exit holes (50) in the base of the column, increases the pressure on the solids as they pass down the column to increase separation efficiency. The pressure can be varied by the speed of the rotation of the auger as well as the pitch of the auger blade and the angle of the cone. The viscosity of the slurry, temperature, and residual solid particle size also affect the transmembrane "filter pressure".

As shown in FIG. 1, the filtered cellulosic solids are suitable for efficient treatment with SSCF. The filtered liquid stream exits the CAFC through the liquid output 40. The alkaline liquid stream should be easily separated by raising the pH to force precipitation of the lignin which can then be filtered, and either fermentation or further separation of the water soluble sugars for ethanol or co-product production.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A process of treating a lignocellulosic material to produce bio-ethanol, the process comprising the steps of:
    (a) grinding a quantity of untreated lignocellulosic material;
    (b) exposing the ground and untreated lignocellulosic material of step (a) to conditions including a pH not less than about 8, and steam at a first pressure, to produce a step (b) product;

(c) explosively discharging the step (b) product to a second pressure less than the first pressure to produce a slurry containing solids; and (d) further processing said slurry by passing said slurry through a device to separate the cellulosic solids from a liquid stream, said device increasing pressure on the separated solids as the solids pass through said device.

2. A process according to claim 1 wherein the first pressure is a pressure of from about 190 psig to about 450 psig, and wherein the second pressure is atmospheric pressure.

3. A process according to claim 1 wherein the pH is not less than about 11.

4. A process according to claim 1 wherein the conditions of step (a) further include a temperature not lower than about 190° C.

5. A process according to claim 1 wherein the conditions of step (a) further include hyperbaric oxygen.

6. A process according to claim 1 wherein the conditions of step (a) further include peroxide.

7. A process according to claim 1 wherein the conditions of step (a) further include a metallic catalyst.

8. A process according to claim 1 wherein the explosive discharge has a Ro of from about 2.5 to about 3.7.

9. A process according to claim 1 wherein step (a) is conducted from a time of from about 1 minute to about 5 minutes.

10. A process according to claim 1 wherein steps (a) and (b) are conducted in a continuous process.

11. A process according to claim 1 wherein the further processing of step (c) includes simultaneous saccharification and co-fermentation.

12. A process of treating a lignocellulosic material to produce bio-ethanol, the process comprising the steps of:
(a) grinding a quantity of untreated lignocellulosic material;
(b) exposing the ground and untreated lignocellulosic material of step (a) to conditions including a pH not less than about 8, and steam at a first pressure, to produce a step (b) product;

(c) explosively discharging the step (b) product to a second pressure less than the first pressure to produce a slurry containing solids; (d) passing the slurry through a fractionation device to separate the cellulosic solids from a liquid stream, the device increasing pressure on the separated solids as the solids pass through the device to increase separation efficiency; and (e) further processing the cellulosic solids and the liquid stream.

13. A process according to claim 12 wherein the fractionation device includes a conical filter through which the slurry is forced to separate the solids from the liquid stream.

14. A process according to claim 13 wherein the fractionation device includes a conical auger inside the conical filter to force the slurry through the filter.

15. A process according to claim 14 wherein the conical auger has an outer diameter which is approximately the same as an inner diameter of the conical filter.

16. A process according to claim 15 wherein the auger turns to displace solids from the surface of the screen and to force material through the conical filter and outlet holes.

17. A process of treating a lignocellulosic material to produce bio-ethanol, the process comprising the steps of:
(a) grinding a quantity of untreated lignocellulosic material; (b) pretreating the ground and untreated lignocellulosic material of step (a) with an alkaline material to raise its pH to not less than about 8; then
(c) exposing the lignocellulosic material to steam at a first pressure to produce a step (c) product; then
(d) explosively discharging the step (c) product to a second pressure less than the first pressure to produce a step (d) product in the form of a slurry having solids; and then
(e) further processing said slurry by passing said slurry through a device to separate the cellulosic solids from a liquid stream, said device increasing pressure on the separated solids as the solids pass through said device.

* * * * *